United States Patent [19]

Jezbera

[11] Patent Number: 4,527,906
[45] Date of Patent: Jul. 9, 1985

[54] DIGITAL MENSTRUAL CYCLE INDICATOR

[76] Inventor: Venda Jezbera, 642 Encino Vista Dr., Thousand Oaks, Calif. 91362

[21] Appl. No.: 453,711

[22] Filed: Dec. 27, 1982

[51] Int. Cl.³ .............................................. G04F 8/00
[52] U.S. Cl. ................................... 368/107; 368/108; 368/89; 368/28
[58] Field of Search ....................... 368/10, 40, 70, 89, 368/107, 108, 109

[56] References Cited

U.S. PATENT DOCUMENTS

| | | | |
|---|---|---|---|
| 4,240,153 | 12/1980 | Merritt | 368/40 |
| 4,244,126 | 1/1981 | James | 368/10 |
| 4,316,276 | 2/1982 | Koehler et al. | 368/70 |

*Primary Examiner*—Bernard Roskoski
*Attorney, Agent, or Firm*—Spensley Horn Jubas & Lubitz

[57] ABSTRACT

Disclosed is a digital menstrual cycle indicator for indicating the fertile portion of a woman's menstrual cycle. A standard watch module that can be continuously operated in a certain adjust mode, has a multidigit display and a clock pulse source, so the module serves as an inexpensive display and clock pulse source. A divider circuit is used to divide the output of the clock pulse source and increment the multidigit display by "1" once each twenty-four hours, after the module has been forced into the adjust mode. A hidden switch is used to force the module into the adjust mode, clear the divider and clear the display. Failsafe circuits are included to prevent the erroneous display of data due to a weak battery or an interruption of the power or ground buses.

1 Claim, 6 Drawing Figures

DIGITAL MENSTRUAL CYCLE INDICATOR

BACKGROUND OF THE INVENTION

1. Field of the Invention

This invention relates to menstrual cycle indicators which provides a visual display of the number of days since the start of a woman's menstrual cycle, and particularly an indicator which uses a digital watch module as the combined day indicator and clock source.

2. Description of the Prior Art

A woman's menstrual cycle is approximately one month long and during a portion that lasts approximately ten days, she is fertile. If the woman wishes to practice the rhythm method of birth control or if she wishes to know on which days she is fertile, she needs some type of method or device to indicate the number of days that have passed since she menstruated.

To date, several methods and devices have been used for determining the number of days that have passed since the start of a menstrual cycle. These methods, however, have a number of drawbacks.

The simplest method is to mark off the number of days on a calendar from the start of the woman's menstrual cycle. This method has two drawbacks. First, the woman must remember to mark off each day as it passes, otherwise she may believe that fewer days have passed from the start of her menstrual cycle. Second, if she incorrectly counts the number of days from the start of her menstrual cycle, she will also make a mistake about the number of days that have passed since the start of her menstrual cycle. A foolproof method is needed so a woman cannot lose track of the number of days since the start of her menstrual cycle. Furthermore, the device should be portable so a woman can take her device with her while traveling and it should also be simple and inexpensive.

Various attempts to achieve these objectives are menstrual cycle indicating devices disclosed in U.S. Pat. Nos. 2,979,884 issued to Gordon, 3,011,303 issued to Dickinson, 3,031,654 issued to Galen, 3,152,437 issued to Vasselli, and 3,472,018 issued to Papworth. These inventions use electromechanical clocks and have a number of drawbacks intrinsic to their designs. A primary drawback is the devices are not portable.

The device disclosed in U.S. Pat. No. 3,031,654 issued to Galen, does contemplate the use of a battery to provide power for an alternative design, but the relatively large amount of power required to drive the motor would dictate the use of a relatively powerful and therefore relatively expensive and bulky battery.

The displays of all of the electromechanical clock menstrual cycle indicators use a combination of hands or dials to display information; in the event of a power failure or some other event that would cause the clock mechanism to malfunction, the unit would still display this information. Therefore, the user could read the displayed information and not realize that the unit has been turned off due to a power failure or some other event. Some devices, U.S. Pat. No. 3,031,654 issued to Galen being typical, do have a light to indicate a power failure. However, if power is turned off and is later applied to the unit, the light, which indicates power is on, would light again so the user would not know that the invention had been turned off for a period of time. Thus, it would still display erroneous data without indicating this to the user.

All the inventions described above include knobs that project out either the front or the rear of the unit for setting or resetting the unit. The drawback of these knobs is that someone could inadvertently reset the unit. This is particularly likely if the clock is accessible to a child.

The device disclosed in U.S. Pat. No. 4,151,831 issued to Lester, uses recorded variations of a woman's temperature during her menstrual cycle to predict when she will ovulate, which is the start of the fertile portion of her menstrual cycle. The drawback of this menstrual cycle indicator is that it is quite complex in that it requires several different pieces of equipment to record the data and perform the necessary calculations to determine the start of the woman's cycle and provide back up storage of the information. This greatly increases the cost of the equipment.

It is therefore an object of the present invention to provide a menstrual cycle indicator that will indicate the number of days that have passed since the start of a woman's cycle and indicate during what portion of the menstrual cycle she is fertile.

It is another object of the present invention to provide a menstrual cycle indicator that is simple to operate, inexpensive and portable.

It is an additional object of the invention to provide a mechanism to prevent the display of erroneous information in case of a failure of the power source of the unit.

It is a further object of this invention to protect the resetting mechanism from inadvertent actuation.

SUMMARY OF THE INVENTION

These and other objects are achieved by using a digital watch module that is operated in the seconds or minutes adjust mode with only two digits of the display of the module shown to the user. This display shows the number of days that have passed since the start of the user's menstrual cycle. A clock pulse source of the watch module is divided down to one pulse per day by a divider circuit; this pulse increments the display by one once every twenty-four hours. The display is set by a switch which is hidden to prevent inadvertent resetting that would cause the indicator to display erroneous information.

The first depression of the switch clears the display and resets the divider. The second depression sequentially causes the divider in cooperation with a control circuit to send sufficient pulses to the watch module to force the module into the minutes or seconds adjust mode, and initiate the display to "01". If the user continues to depress the switch during the second actuation rather than immediately releasing it, the divider will send pulses to the watch module to increment the display by one every few seconds until the switch is released. This allows the user to set the display of the watch to any date less than 60.

Because the watch display may continue to show data when the divider or control circuits are not functioning properly due to an undervoltage condition or an interruption of the power or ground buses, the menstrual cycle indicator includes three fail-safe circuits to prevent the display of erroneous data. An undervoltage circuit is included to detect the drop of the indicator's power source voltage below a specified level. Other circuits detect an interruption of the power or ground buses. Upon detecting these conditions, the circuits cause the divider to be cleared and shut off the display.

DESCRIPTIONS OF THE PREFERRED EMBODIMENT

The following description is the best presently contemplated mode of carrying out the invention. This description is made for the purpose of illustrating the general principles of the invention and is not to be taken in a limiting sense. The scope of the invention is best determined by the appended claims.

Figure 1:
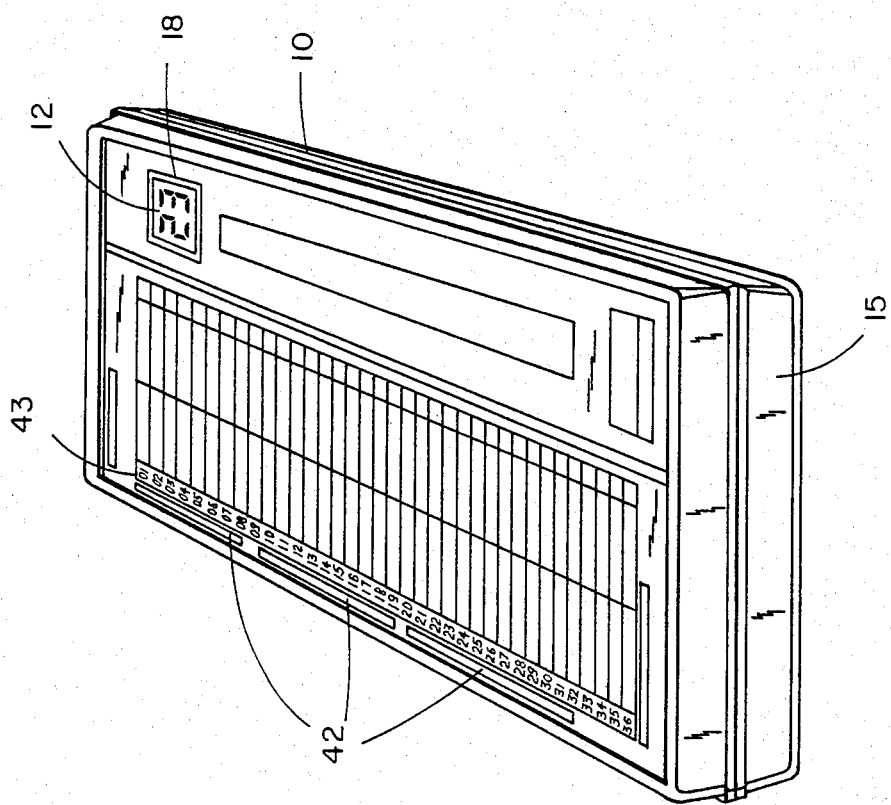
FIG. 1 is a top perspective view of the menstrual cycle indicator.
Figure 2:
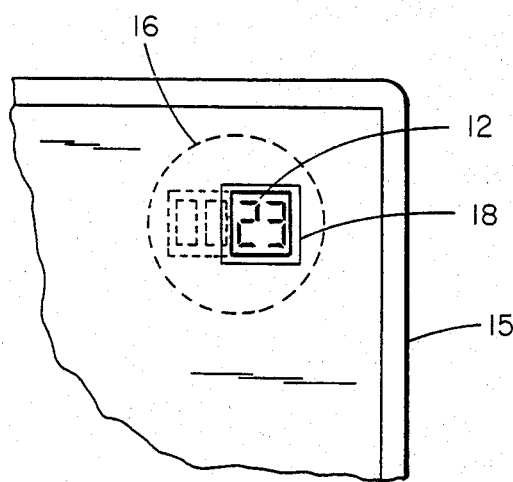
FIG. 2 is an enlarged view of the menstrual cycle indicator of FIG. 1 as seen in the region of the display.
Figure 3:
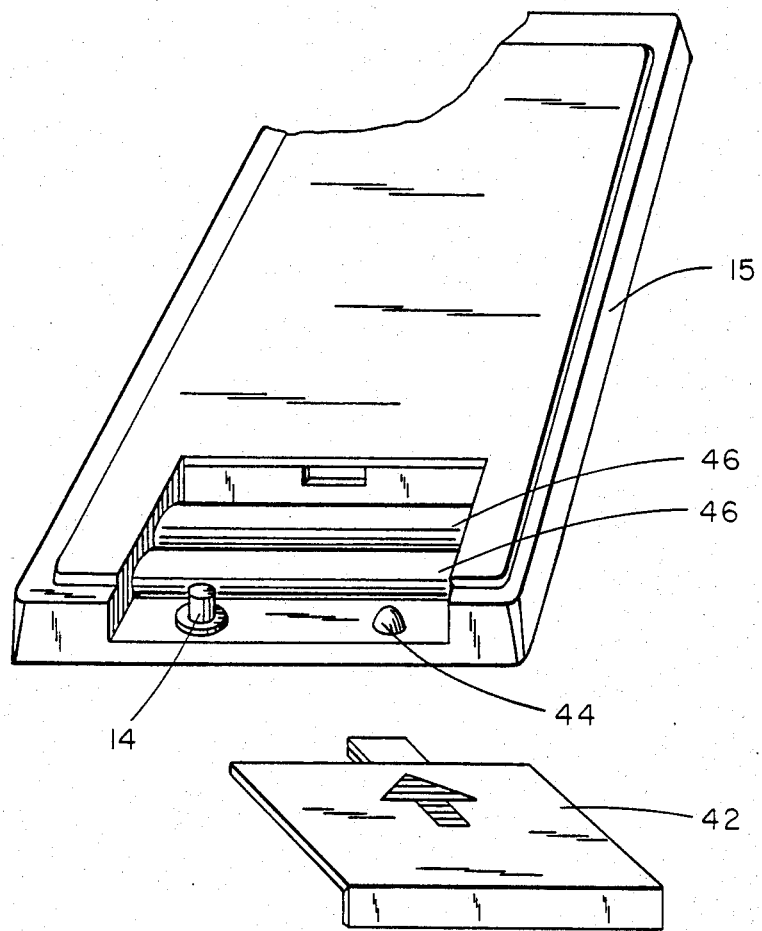
FIG. 3 is a perspective view of the bottom of the menstrual cycle indicator with the battery case cover removed.

Referring to FIGS. 1-3, there is shown a digital menstrual cycle indicator 10 in accordance with the present invention. The indicator includes a display 12 which indicates the number of days that have elapsed since the beginning of the menstrual period. This display is reset to "01" when a pushbutton 14 located beneath a battery case cover 42 on the rear of a housing 15 (FIG. 3) is depressed twice. Thereafter, the display 12 is incremented automatically by one as each day elapses. The pushbutton 14 is hidden inside the indicator housing 15 so that it will not be accidentally depressed, with concomitant erroneous resetting of the display 12.

In accordance with the present invention, the display 12 is part of a conventional watch module 16 (FIG. 2), which also serves as the clock pulse source for the device. A window 18 in the housing 15 exposes to view only the two rightmost digits of the watch module display. These are the digits that typically are used to display the minutes, seconds or date, depending upon the mode of operation of the module 16. The leftmost display digits, which typically are used to indicate the hour or month, are hidden from view behind a portion of the housing 15.

In the present invention, the watch module 16 is not operated in the conventional time keeping mode. Rather, it is continuously operated in the "adjust" mode in which the rightmost digits are incremented by one each time an "adjust" pulse is supplied to the module 16. This is the mode which during conventional watch operation is used to increment the seconds or minutes usually each time a pushbutton is depressed. For use in the present invention, the watch module 16 should be configured so that it can remain in the "adjust" mode indefinitely, and will not automatically revert back to a normal timekeeping mode. By way of example, the Motorola type MC 14440 LSI LCD watch/clock circuit may be used. In the present invention, the module 16 is set into the adjust mode by two depressions of the switch 14.

Figure 4:
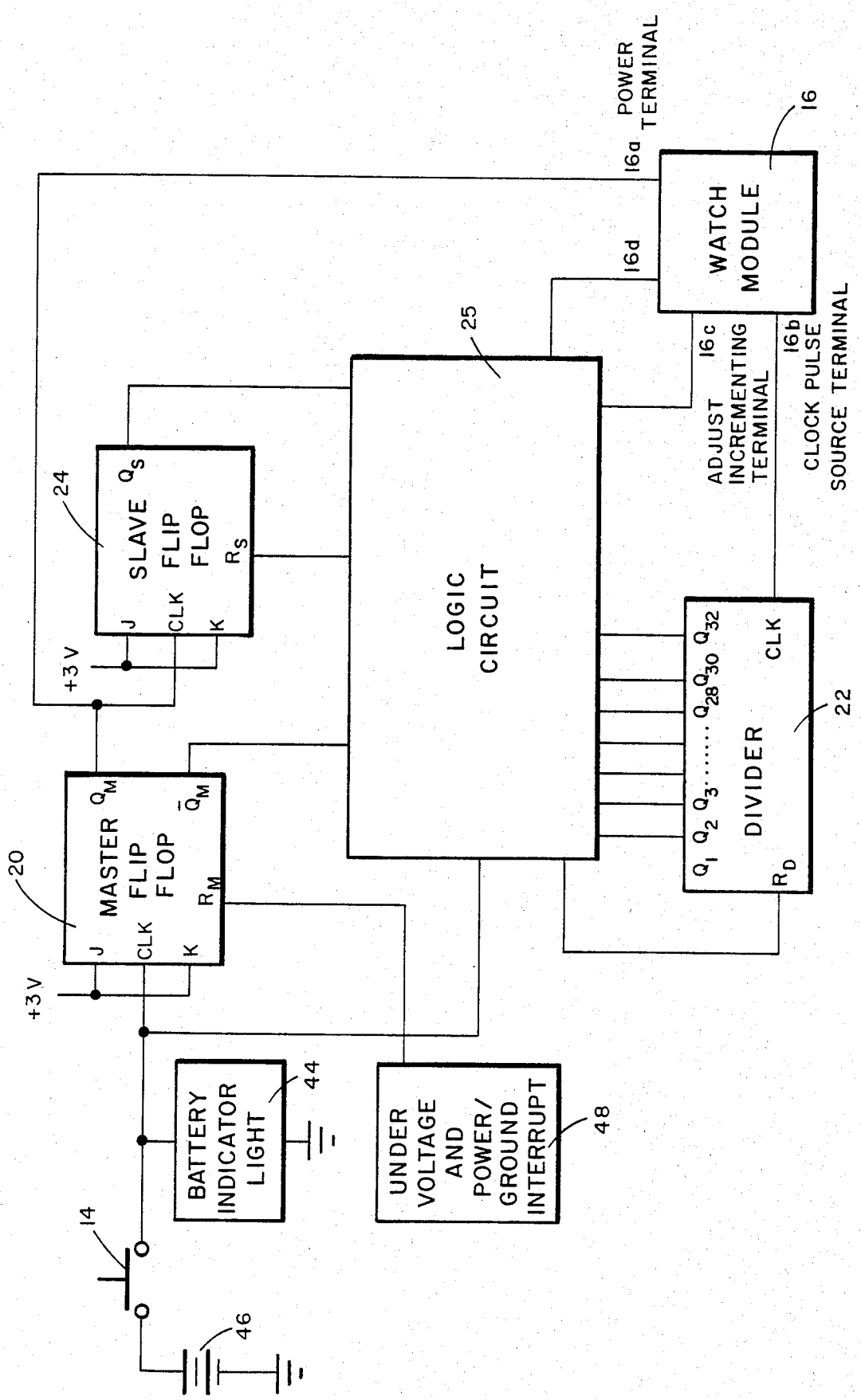
FIG. 4 is block diagram of the electronic circuits of the menstrual cycle indicator.
Figure 5:
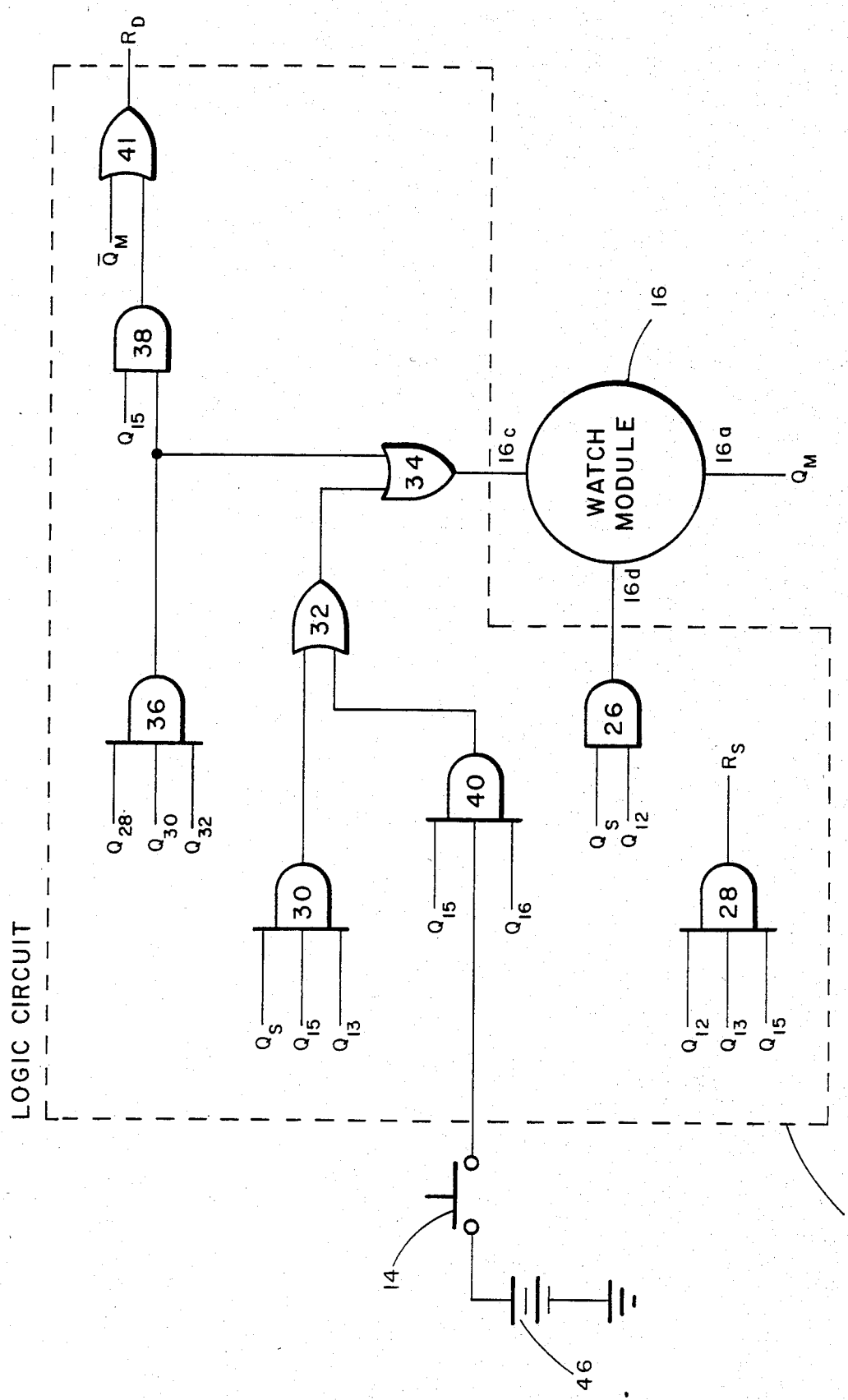
FIG. 5 is a schematic of the control circuit shown in FIG. 4.

Referring now to FIGS. 4 and 5, the means for resetting the display, forcing the watch module into the adjust mode and incrementing the display by depressing the push button are shown. The first time the reset button 14 is depressed, the clock pulse source in the watch module 16 is interrupted, the display 12 is cleared, and the divider circuit 22 is reset.

The first depression of the reset button 14 accomplishes these functions by resetting a master flip-flop 20. The output $Q_m$ of the master flip-flop 20 goes low and provides a low signal to the power terminal 16a of the watch module 16. This low signal clears the display 12 and interrupts the clock pulse source of the watch module 16, which pulses at approximately 32,768 Hz. The clock pulse source terminal 16b is connected to the clock input of a divider 22 where it is divided down to provide the one pulse per day to the adjust incrementing terminal 16c of the watch module 16 to increment the display. The inverted output of the master flip-flop 20 ($\overline{Q}_m$), which goes high on the first depression of reset button 14, resets the divider 22 to zero by providing a high to the reset input $R_D$ of the divider through a logic circuit 25.

The divider 22 has thirty-two outputs $Q_1$ through $Q_{32}$. The subscript n of $Q_n$ denotes that that output is pulsing at the clock pulse source's rate divided by 2 to the $n^{th}$ power. Thus $Q_1$ pulses at approximately 32,768 Hz divided by 2, while $Q_{12}$ pulses at approximately 32,768 Hz divided by 4096.

The next depression of the reset button 14 starts the clock pulse source, forces the watch module into the desired adjust mode, and sets the display to the number of days that have passed since the start of the menstrual cycle. The second depression of the reset button 14, sets the master flip-flop 20, which in turn sets a slave flip-flop 24, causing its output $Q_s$ to go high. The output $Q_s$ is used to activate those portions of the logic circuit 25 that force the watch module into the adjust mode and initiate the display 12 to "01".

Referring now to FIG. 5, AND gate 26 provides the pulses to force the watch module into the desired adjust mode. AND gate 26 is turned on by $Q_s$. When AND gate 26 is turned on by $Q_s$, the mode setting terminal 16d is pulsed every time $Q_{12}$ pulses, which is the other input of AND gate 26.

When the required number of pulses to force watch module 16 into the desired adjust mode have been sent, AND gate 26 must be turned off by forcing $Q_s$ low. This is accomplished by providing a high level on the slave flip-flop 24 reset input $R_s$ through AND gate 28. AND gate 28 is turned on when $Q_{12}$, $Q_{13}$ and $Q_{15}$ go high. These outputs of the divider have been chosen because they will cause the slave flip-flop 24 to reset only when the mode setting terminal 16d has been pulsed the required number of times to force the watch into the desired mode. No more pulses will appear on the mode setting terminal 16d until $Q_s$ again goes high.

While $Q_s$ is still high, the adjust incrementing terminal 16c must be pulsed once to initiate the display 12 to "01". This is accomplished by activating AND gate 30 by $Q_s$. The other inputs of AND gate 30 are $Q_{13}$ and $Q_{15}$ so AND gate 30 will be pulsed once before $Q_s$ goes low due to the resetting of the slave flip-flop 24. This pulse is passed to the adjust incrementing terminal 16c through OR gates 32 and 34 to increment the display.

During normal operations the display 12 of the watch module 16 is incremented once every 24 hours by a pulse from AND gate 36 through OR gate 34 to the adjust incrementing terminal 16c. The inputs of AND gate 36 are $Q_{28}$, $Q_{30}$, and $Q_{32}$, which have been selected because they will all be high once every 24 hours.

Therefore, AND gate 36 will pulse once every 24 hours.

In order to ensure that the adjust incrementing terminal 16c is not pulsed for another twelve hours after AND gate 36 has pulsed the terminal 16c, the divider must be reset after the adjust incrementing terminal has been pulsed. Therefore, the output of AND gate 36 and $Q_{15}$ of the divider are combined at AND gate 38 and passed through OR gate 41 to the reset $R_D$ of the divider 22. This resets the divider 22 so the divider starts counting pulses and the adjust incrementing terminal 16c will not be pulsed again until another 24 hours have gone by at which time the display 12 will be incremented.

If the user desires to set the display 12 to a date beyond "01", the user must merely continue to depress the push button 14 during its second actuation instead of immediately releasing it. While the push button is depressed, AND gate 40 is activated. The other inputs of AND gate 40 are $Q_{15}$ and $Q_{16}$ so the output of AND gate 40 will go high whenever $Q_{15}$ and $Q_{16}$ are both high. The output of AND gate 40 pulses the adjust incrementing terminal 16c via OR gates 32 and 34 to increment the display.

By reading the number in the display 12, the user knows the number of days that have passed since the start of the menstrual cycle. As shown in FIGS. 1 and 2, the display 12 of the watch module 16 can be seen through the window 18 on the top of the housing 15. Along one edge of the top of the housing 15, is a column of numbers 43 ranging from "01" through "36". Different colored tapes 42 can be affixed to the top of the housing, adjacent to the column of numbers 43, to indicate the fertile and infertile portions of a woman's menstrual cycle. By comparing the number displayed in the window 18, with the column of numbers marked off with tape, the user can determine whether the date shown is within the fertile portion of her menstrual cycle.

There are a number of fail-safe features on this digital menstrual cycle indicator. These include a hidden reset button 14 to prevent accidental actuation of the system, a battery voltage light, an undervoltage protection and power and ground bus interrupt circuits to prevent erroneous display of information.

If the reset pushbutton 14 were accidentally depressed, erroneous information could be displayed. Therefore, referring now to FIG. 3, the reset button 14 is hidden within the housing 15 by the battery case cover 42, which is force-fit into the housing 15. The battery case cover 42 covers a space inside the housing 15 containing batteries 46, which power the indicator, an indicator light 44 and the reset button 14. Only by forcibly removing the battery case cover 42 is the reset pushbutton 14 accessible.

A battery indicator light 44 is provided to inform the user when the voltage level of the batteries 46 is too low. Whenever the reset button 14 is depressed, the battery indicator light 44, which is a photoelectric diode (FIG. 4) connected from the output of the reset button 14 to ground, will measure the voltage level of batteries 46. The diode circuitry is selected so that it will only emit light if the voltage level is greater than a specified level. If the light 44 fails to emit light, the user is informed that the batteries may need replacement.

Another fail-safe feature of the present invention concerns the fact that the LCD display 12 may operate at a lower voltage than is required to operate the divider 22. Thus, it may happen that the battery voltage drops to a level at which the display continues to operate, but below the level the divider needs to operate. In such a situation, the display will not be incremented at the end of each 24-hour period, so the indicated number of days since menstruation may be incorrect.

Figure 6:
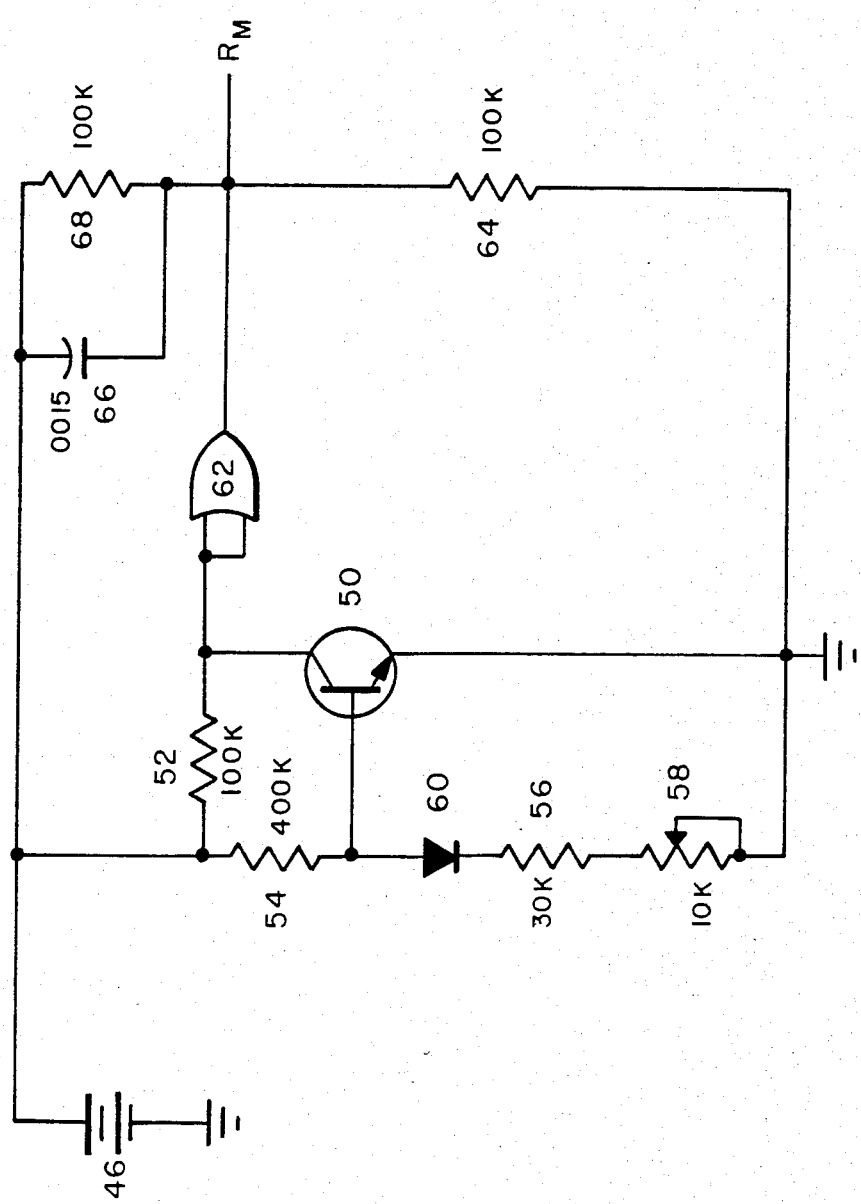
FIG. 6 is a schematic of an undervoltage detection and power/ground interrupt detection circuit shown in FIG. 4.

To avoid this undesirable situation, an undervoltage detection circuit 48 is provided. This circuit detects when the battery voltage has dropped below the level required to operate the divider 22. Whenever this occurs, the circuit 48 turns off the display 12 so erroneous data is not shown. FIG. 6 is a detailed schematic of the undervoltage detection circuit. The transistor 50, resistors 52, 54, 56 and 58 and the diode 60 are used to detect whenever the voltage of the power source 46 drops below a level that may cause the system to display erroneous information. In normal operations, the transistor 50 is conducting current from the collector to the emitter so that the voltage appearing across the transistor is low enough for a logical "0" to be detected by the input of the OR gate 62. Therefore, the output of OR gate 62 is a "0" so a "0" will appear at the master flip-flop's reset 20. If the voltage supplied by the batteries 46 drops below the specified point, the diode 60 will stop conducting, shutting off the transistor 50, so there will be a voltage drop across the transistor sufficient to cause the OR gate 62 to detect a "1". The OR gate 62 will therefore place a "1" at the reset input of the master flip-flop 20. This has the same effect as the first depression of the reset button 14 so the display 12 will be cleared and the clock pulse source is deactivated.

A further fail-safe feature of the present invention concerns the possibility of an interruption of the power or ground buses of the digital menstrual cycle indicator or the removal of the batteries 46. If the ground connection between the batteries and the remainder of the device is broken, the resistor 64 will effectively be disconnected from the circuit so there will be no voltage drop across the resistor 64. Therefore, a high positive voltage will appear at the reset of the master flip-flop 20. This voltage will reset the master flip-flop, having exactly the same effect as the first depression of the reset button 14, thereby clearing the divider circuit and the display 12.

The capacitor 66 and the resistor 68 are used in conjunction with the circuit described above to detect any interruptions of the power bus or the connection between the power bus and the batteries. If there is such an interruption from the power source 46, the capacitor 66 will provide sufficient electrical energy to the circuit to provide an impulse of logical "1" to the reset of the master flip-flop, thereby clearing the divider 22 and the display 12.

In summary, a digital menstrual cycle indicator for determining when a woman is in the fertile portion of her menstrual cycle is disclosed. To lower the cost of the unit, a standard watch module is utilized for a display, and this watch module is used in the minutes or seconds setting function. The hidden actuation switch is used to avoid the possibility of accidental resetting of the device. An undervoltage and power and ground interrupt circuit is provided to prevent the digital menstrual cycle indicator from displaying erroneous information.

I claim:
1. A menstrual cycle indicator, comprising:
   a watch module having a multidigit display and a clock pulse source, and continuously operable in a certain adjust mode in which pulses supplied to the module will increment the display, a reset switch;

control means, operable in response to actuation of said reset switch, for clearing the display, for switching said module to said certain adjust mode, and, while said module is operating continuously in said adjust mode, for supplying divided pulses from said clock pulse source to said module to increment the display by "one" for each day period, thereby facilitating indication of the day of the menstrual cycle, timekeeping inhibit means, cooperating with said control means, for continually preventing said watch module from operating in the normal timekeeping mode, a power source, said display being operable at a lower voltage than said divider, and a failsafe circuit comprising:

means for detecting the decrease of the power source voltage below the voltage level required to operate the divider;

means for clearing the display of the watch module and resetting the divider in response to such detection, whereby the display of erroneous data is prevented, together with;

a housing for the digital menstrual cycle indicator wherein the housing has a cavity;

a cover for the cavity;

said reset switch being situated in the cavity concealed by the cover, thereby preventing accidental actuation of the reset switch.

* * * * *